United States Patent [19]

Sivasanker et al.

[11] Patent Number: 5,453,553
[45] Date of Patent: Sep. 26, 1995

[54] PROCESS FOR THE PRODUCTION OF LINEAR ALKYLBENZENES

[75] Inventors: Subramanian Sivasanker; Paul Ratnasamy, both of Maharashtra, Ind.

[73] Assignee: Council of Scientific & Industrial Research, New Delhi, Ind.

[21] Appl. No.: 176,504

[22] Filed: Dec. 30, 1993

Related U.S. Application Data

[63] Continuation of Ser. No. 863,950, Apr. 3, 1992, abandoned.
[51] Int. Cl.$^6$ ....................................................... C07C 2/66
[52] U.S. Cl. ................................................................ 585/467
[58] Field of Search ............................................. 585/467

[56] References Cited

U.S. PATENT DOCUMENTS

| | | | |
|---|---|---|---|
| 4,049,739 | 9/1977 | Zabramsky et al. | 585/467 |
| 4,301,317 | 11/1981 | Young | 585/467 |
| 4,891,458 | 1/1990 | Innes et al. | 585/323 |
| 4,962,256 | 10/1990 | Le et al. | 585/467 |
| 5,034,563 | 7/1991 | Ashjian et al. | 585/467 |
| 5,118,897 | 6/1992 | Khonsari et al. | 585/467 |

FOREIGN PATENT DOCUMENTS

| 160144 | 11/1985 | European Pat. Off. | 585/467 |
|---|---|---|---|

*Primary Examiner*—Asok Pal
*Attorney, Agent, or Firm*—Ladas & Parry

[57] ABSTRACT

The invention discloses a process for production of linear alkylbenzenes which comprises contacting a mixture of benzene linear olefins and hydroen with a catalyst containing a transition metal like iron, cobalt, nickel, platinum, palladium, iridium or mixtures thereof in intimate contact with a zeolite such as mordenite, beta X, Y or ZSM-12 and separating the linear alkylbenzenes from the reactor effluents. The present invention introduces the manufacture of LAB using solid catalyst under condition wherein the catalyst is not deactivated and hence leading to normal operation cycle lengths between successive regeneration which are substantially longer than those in prior art.

9 Claims, No Drawings

PROCESS FOR THE PRODUCTION OF LINEAR ALKYLBENZENES

This is a continuation of application Ser. No. 07/863,590, filed on Apr. 3, 1992, now abandoned.

This invention refers to a process for the production of linear alkylbenzenes. More specifically it refers to a novel process for the alkylation of benzene with linear olefins containing from 8 to 20 carbon atoms to linear alkylbenzenes in the presence of hydrogen using a catalyst.

BACKGROUND OF THE INVENTION

Linear alkylbenzenes (LAB) have been the surfactant of choice because they are cost effective and biodegradable. Sulfonates of LAB are the main ingredients in detergent powders. In the present day art, LABs are manufactured by the alkylation of benzene by linear olefins in the presence of HF acid. U.S. Pat. Nos. 3,494,970 and 3,830,865 describe a process for the production of LAB using HF catalysts. U.S. Pat. Nos. 3,631,123 and 3,674,885 and 3,703,559 describe the use of other Lewis acid catalysts such as $AlCl_3$ in the production of LAB. In addition to the use of the above liquid phase acid catalysts, solid acid catalysts such as clays and zeolites have also been used in the production of LAB. U.S. Pat. No. 4,459,426 describes the use of zeolites as the catalysts for the alkylation of benzene with light $C_2$–$C_4$ olefins. Due to the narrow size of the zeolite pores, they do not allow the diffusion of heavy olefins. Thus the alkylation in the presence of the said zeolites can only be carried out with light olefins. U.S. Pat. No. 3,849,507 describes the use of a clayish material activated with mineral acids and subsequently made into pellets for alkylation of benzene with olefins with 4 to 8 carbon atoms per olefin molecule. U.S. Pat. No. 4,046,826 uses a natural or synthetic trioctahedral clay, hectorite type, interchanged with metallic cations for the alkylation of benzene with heavy olefins, basically 1-dodecene. European Patent application 83970 uses for the alkylation of benzene with light olefins a clay in which pillars of alumina have been anchored inside its laminar structure, as catalyst. U.S. Pat. No. 3,417,148 refers to the use of a crystalline aluminosilicate chemically combined with metallic subfluoride as a catalyst for the production of alkylbenzenes. U.S. Pat. No. 4,070,407 and assigned to Mobil Oil Co. describes the use of a crystalline aluminosilicate zeolite as a catalyst for the alkylation of benzene with olefins, alcohols and alkyl halides to produce alkylbenzenes. European Patent application Eu.0,353,813 A1 describes a process for the alkylation of benzene with $C_2$–$C_{20}$ mono-olefins in the presence of an aluminium-magnesium silicate catalyst to give LAB of detergent range. The process is continuously carried out in a fixed bed, the alkylation taking place in the liquid phase.

In the present art, the process using liquid HF acid as the alkylation catalyst is in commercial practice in most of the plants all around the world. In the process developed by E. R. Fenske, U.S. Pat. No. 3,494,971 assigned to UOP Company, the alkylation takes place in successive steps and uses HF as a catalyst either fresh and/or regenerated depending on the different steps of the process. The feeding of liquid hydrocarbons (10 to 15 carbon atoms per molecule) is made up of a mixture of an excess (90%) of non-dehydrogenated linear hydrocarbons alone with a minor olefin fraction (10%) with approximately 95% mono-olefins and 5% diolefins. Benzene is in molar excess over the mono-olefin fraction. Two phases are obtained as the reaction product, the one which contains the alkylation catalyst and the other one that contains the hydrocarbons. From the reaction product the HF catalyst is separated/partly regenerated and recycled. Benzene is also separated and recycled to the alkylation reactor. The unreacted linear paraffins are separated from the LAB and recycled to the dehydrogenation reactor for partial conversion to linear olefins.

There are a few limitations in the prior-art processes using liquid phase acid catalysts such as HF, $AlCl_3$ etc. One limitation is the corrosive nature of these acids leading to laborious and costly procedures and equipment for their handling. A second limitation is the environmental hazards in the handling and disposal of the spent HF catalyst. A third limitation is the toxicity of the HF acid to the plant personnel in case of leaks due to accidental plant upsets.

The use of prior-art solid acid catalysts such as zeolites and clay material also has limitations. A major limitation in the use of such catalysts is the very short cycle length between regenerations necessitating frequent interruptions in the production of LAB. For example, in the European Patent application EU 0,353,813 assigned to Petrosa, Example 1 cites the normal operating cycle length of the catalyst as 12 hrs. The regeneration of the catalyst is carried out in a semi-continuous manner making alternating and successive currents of paraffins and alcohols pass through the catalyst in cycles. The duration of the regeneration cycle was cited as 6 hrs.

In view of the above, it was the objective of the work leading to the present invention to discover a process for the manufacture of LAB using solid catalysts under conditions wherein the catalyst is not deactivated and hence leading to normal operating cycle lengths between successive regenerations which are substantially longer than those prevailing in the prior-art.

SUMMARY OF THE PRESENT INVENTION

The present invention consists of a process for the manufacture of linear alkylbenzenes by reacting benzene with linear olefins in the presence of hydrogen using a solid catalyst which consists of a zeolite material containing transition metals. The novelty of the invention resides (1) in carrying out the alkylation process in the presence of hydrogen and (2) in the use, as catalysts, of typical solid acid catalysts such as zeolites, *in intimate combination* with typical hydrogenation catalysts such as transition metal elements. The process is carried out continuously. The feed to the reactor consists of a mixture of benzene and linear olefins. The olefins may be diluted with linear paraffins. The benzene to olefin molar ratio may range from 2 to 20. The carbon numbers of the olefins may range from 8 to 20. The process is carried out at a temperature in the range of 100° to 200° C., a pressure in the range of 1 to 20 bar and a liquid hourly space velocity of 1 to 10. Molar ratios of hydrogen to olefin in the range of 1 to 5 may be utilised. Under the above conditions, all the linear olefins in the feedstock are substantially converted to LAB. The outlet from the alkylation reactor is processed further to recover LAB by conventional methods. This is done by first separating hydrogen gas from the liquid and recycling it to the inlet of the alkylation reactor, unreacted benzene and linear paraffins are next separated by fractional distillation. The benzene is recycled back to the alkylation reactor. The paraffin is recycled to the dehydrogenation reactor. Pure LAB is recovered from the bottoms of the paraffin separation column by fractional distillation.

DETAILED DESCRIPTION OF THE INVENTION

The present invention consists of a process for the alkylation of benzene with a linear olefin in the presence of hydrogen which comprises the separation of the alkylation reaction product into (1) a hydrogen fraction (2) a benzene fraction (3) a paraffin fraction (4) a linear monoalkylbenzene fraction and (5) a heavy alkylbenzene fraction, the recycling to the process of the hydrogen, paraffin and benzene fractions and the separation of an essentially pure linear monoalkyl benzene using as an alkylation catalyst a solid material which consists essentially of a zeolite containing transition metals in intimate interaction with the said zeolite.

According to the process of the present invention the use of hydrogen in an alkylation reaction of benzene with an olefinic compound gives an alkylbenzene product, which is a typical acid catalysed reaction.

Further in the process of the present invention a solid material containing transition metals is being used as an alkylation catalyst of the said transition metals being normally used as catalysts mainly in hydrogenation and oxidation catalysts and not as catalysts for a typical acid catalysed reaction such as the alkylation of benzene with olefins to alkylbenzenes.

More essentially in the present invention that when the alkylation reaction is carried out in the presence of hydrogen and using transition metals as essential ingredients of the zeolite catalyst, the novel and desirable advantages of the process of the present invention are manifested. These latter advantages are not obtained when the process is carried out over the zeolite catalysts containing transition metals but in the absence of hydrogen. Nor are they observed when the process is carried out in the presence of hydrogen over zeolite catalysts which do not contain the transition metal elements as essential ingredients.

The zeolites that may be used as alkylation catalysts may be chosen from those that have the lattice framework structure of zeolites such as x, y, mordenite, ZSM-12 or beta. The manufacture of these zeolites is well known to those skilled in the prior-art. Zeolites containing transition metals, like iron, as lattice components are also well known in the prior art (For a recent review, see Catalysis Today, Vol. 9, No.4 (1991), Elsevier Publishers). Zeolites are acidic solids due to the presence of protons in their structure. Their use as active catalysts in acid catalysed reactions like hydrocarbon cracking, isomerisation and alkylation are well known.

In the prior-art, when zeolites are used as catalysts in alkylation processes, such as the process of the present invention, the process is invariably carried out in the absence of added molecular hydrogen. The alkylation of benzene with ethylene to produce ethylbenzene and the alkylation of benzene with propylene to cumene are examples of two such processes carried out in the absence of hydrogen. U.S. Pat. No. 4,891,458 describes, for example, the alkylation of aromatic hydrocarbons with $C_2$ to $C_4$ olefins in the presence of zeolite catalysts. The reason for the non-utilisation of hydrogen in alkylation reactions is that in such processes acidic protons present in the catalyst structure play the role of active sites catalysing the alkylation reactions and the use of hydrogen does not confer any benefits to the practice of such processes. The presence of hydrogen usually confers significant advantages mainly in processes like hydrogenation, which do not involve the acidic protons of the catalyst as active sites.

It was hence, a surprising and unforeseen result during the course of the investigations leading to the present invention that the presence of hydrogen prolonged significantly the useful life of the catalyst when zeolite catalysts containing certain transition metals in intimate contact with the said zeolite structure were used as catalysts in the process of alkylation of benzene with linear olefins to LAB.

Preferably, the zeolite may be chosen from the group x, y, mordenite, ZSM-12 or beta. Zeolite x is described in U.S. Pat. No. 2,882,244. Zeolite y is more fully described in U.S. Pat. No. 3,130,007. Mordenite is described in U.S. Pat. No. 4,377,502. ZSM-12 is described in British Patent GB 1572135. Zeolite beta is described in U.S. Pat. No. 3,308,069.

Further, the transition metals in the catalyst used in the process may constitute iron, cobalt, nickel, platinum, palladium, iridium or mixtures of the above. The transition metals may occur either in zeolite lattice framework positions or occluded within the porous cavities of the zeolites in cation-exchange positions. Zeolites containing transition metals in lattice framework positions are well known in prior-art (For a recent review, see Catalysis Today, Vol. 9, No. 4, P.329 (1991).

In the prior-art, when zeolite containing catalysts were used in the alkylation of benzene with linear olefins to produce linear alkylbenzenes, the major limitation was that the catalysts were deactivated at a very fast rate within a few hours rendering the process economically unviable.

According to the present invention, the catalyst used in the process retains its initial activity and selectivity for more than a month thereby rendering the process of this invention much superior to those hitherto known in the prior-art. The precise origin of the surprising and beneficial effect of carrying out the alkylation reaction in the presence of hydrogen over zeolites containing transition metals in intimate contact with the said zeolites according to the present invention is not known in detail at present. It is, however, probable that since the deactivation of the zeolite catalysts observed in the prior-art processes is mainly due to carbonaceous deposits, the formation of such deposits is suppressed when the same alkylation is carried out in the presence of hydrogen over zeolites containing transition metals according to the present invention.

More importantly in the present invention that while the formation of carbonaceous deposits is suppressed by hydrogenation of the precursors of such deposits like diolefins, the linear olefins which are the alkylating agents leading to the formation of linear alkylbenzens are not hydrogenated at all. Moreover, the transition metals present on the catalyst occur in such an active state that they hydrogenate the precursors of carbonaceous deposits without simultaneously hydrogenating the linear olefins to linear paraffins or cracking them to hydrocarbons with a lower carbon number.

Further in the present invention the hydrogenation and acidic activity of the catalyst used in the process are optimally balanced so that the catalyst possesses adequate acidic property to alkylate the benzene with linear olefins to yield linear alkylbenzene as well as optimal hydrogenation activity to hydrogenate only the coke precursors without hydrogenating the linear mono-olefins which are the needed alkylating agents to obtain the LAB.

For use in the process of this invention the zeolite catalyst containing transition metals can be formulated with conventional binders like silica, alumina, clays etc into a suitable form like cylindrical extrudates, spheres etc, to improve the mechanical strength of the catalyst particles.

The process may be conventionally carried out in a fixed bed adiabatic reactor. The benzene feed should be present in stoichiometric excess. It is preferred that the molar ratio of benzene to the linear olefins be at least five to one to prevent rapid catalyst fouling. The reaction temperature may range between 100° and 200° C. The reaction pressure should be sufficient to maintain at least a partial liquid phase in order to retard catalyst fouling. This is typically 1 to 20 bar ad preferably 5 to 20 bar. The liquid hourly space velocity, in terms of total liquid volume of feed passed per hour per unit volume of catalyst is generally within the range of about 1.0 to 10.

Preferably in the present invention, the alkylation process is carried out with the addition of the linear olefin in at least two stages. Preferably, there will be two or more catalyst beds or reactors in series wherein at least a portion of the olefin is added between the catalyst beds or reactors. Interstage cooling can be accomplished by the use of a cooling coil or heat exchanger.

The alkylation reactor effluent contains hydrogen, excess benzene, paraffins the linear monoalkylbenzenes, polyalkylated products and various impurities. The hydrogen, benzene and paraffins are first recovered and recycled to the alkylation reactor. The bottoms from the paraffin distillation may be further distilled to separate the LAB from polyalkylated products and other heavies. The recovered LAB is very pure and meets the required specifications of Bromine Index (BI).

The process of the present invention is illustrated with the following examples which are only illustrative in character.

EXAMPLE 1

The alkylation of benzene with linear olefins to form linear alkylbenzenes (LAB) was carried out in a down-flow integral reactor of 220 ml volume. The mixture of hydrogen, benzene and the olefins was metered in through automated flow and pressure control values. The olefin feed was obtained from a commercial LAB plant and contained about 8% wt. of linear olefins with carbon numbers between 9 and 14 and 92% wt. of linear paraffins in the same carbon number range. This olefin feed was obtained from the outlet of the paraffin dehydrogenation unit. The liquid hourly space velocity (LHSV) is defined as the volume of liquid (benzene+olefin feed) passing through unit volume of the catalyst bed per hour. The reactor was operated in the isothermal mode. The examples illustrate the performance of the various catalysts under different operating conditions. The latter was judged from the Bromine Index (BI) of the product and the LAB content. The higher the BI, the higher is the concentration of the unreacted olefin in the product and the lower is the performance rating of the catalyst. The reaction variables studied were temperature, pressure, LHSV, benzene to linear olefin molar ratio (B/O) and hydrogen to benzene molar ratio (H/B).

A H-ZSM-12 zeolite of Si/Al=40 was impregnated with 0.1% wt of various transition metals and extruded with a boehmite binder, calcined at 450° C. in air and reduced in hydrogen at 400° C. to yield the final catalyst. 100 g of the catalyst was used in each experiment. Products were analysed after 100 hrs of time-on-stream.

TABLE 1

| Catalyst | T°C. | Press bar | LHSV | B/O | H/B | BI |
|---|---|---|---|---|---|---|
| Pt-ZSM-12 | 120 | 20 | 6 | 10 | 3 | 105 |
| Ni-ZSM-12 | 120 | 10 | 2 | 10 | 3 | 205 |

TABLE 1-continued

| Catalyst | T°C. | Press bar | LHSV | B/O | H/B | BI |
|---|---|---|---|---|---|---|
| Co-ZSM-12 | 120 | 15 | 2 | 10 | 3 | 210 |
| Pd-ZSM-12 | 130 | 20 | 4 | 10 | 3 | 100 |
| Iv-ZSM-12 | 150 | 20 | 6 | 10 | 3 | 165 |

EXAMPLE 2

The experiments in Example 1 were repeated using ferrisilicate analogs of ZSM-5, beta, mordenite and Y zeolites. The results are shown in Table 2. The (H/B) was held constant at 5.

| Catalyst | Si/Fe | T°C. | Press. bar | LHSV | B/O | BI |
|---|---|---|---|---|---|---|
| Pt—Fe-ZSM-12 | 40 | 110 | 8 | 3 | 8 | 800 |
| Pt—Fe-beta | 62 | 120 | 10 | 2 | 10 | 750 |
| Pd—Fe-Mord | 15 | 140 | 15 | 1 | 12 | 1650 |
| Pt—Fe-X | 8 | 150 | 15 | 3 | 10 | 45 |
| Pd—Fe-Y | 8 | 125 | 20 | 1 | 10 | 88 |
| Ni—Fe-beta | 62 | 135 | 20 | 4 | 15 | 1153 |

EXAMPLE 3

The experiments in Example 1 were repeated with a rare-earth containing zeolites Y, beta and mordenite. The rare-earth was lanthanum oxide and its content was between 2 and 15% wt depending on the zeolite. The results are given in Table 3.

| Catalyst | Si/Al | Re content | T°C. | Press. bar | LHSV | B/O | BI |
|---|---|---|---|---|---|---|---|
| Pt-Y | 5 | 15.0 | 120 | 10 | 2 | 10 | 40 |
| Pt-beta | 54 | 2.3 | 130 | 8 | 2 | 10 | 254 |
| Pd-mord. | 15 | 1.1 | 120 | 12 | 1 | 10 | 450 |
| CO-Y | 5 | 14.7 | 135 | 10 | 1 | 8 | 88 |
| Ni-beta | 54 | 2.3 | 125 | 15 | 2 | 8 | 52 |
| Co-beta | 54 | 2.3 | 125 | 15 | 2 | 8 | 618 |
| Ir-Y | 5 | 15.0 | 120 | 10 | 1 | 8 | 58 |
| Pd-Y | 5 | 13.8 | 120 | 10 | 1 | 10 | 48 |

EXAMPLE 4

A series of transition metal loaded zeolite based catalysts containing 0.1 wt. of the transition metal were prepared wherein the transition metal was incorporated in intimate contact with the zeolite component by including the former in the reaction mixture used in the synthesis of the zeolite. Both alumino and ferrisilicate analogs of the zeolite containing the transition metals were thus prepared and evaluated as in Example 1. The H/B was held constant at 2 and the pressure was 10 bar.

| Catalyst | Si/Al | Si/Fe | T°C. | LHSV | B/O | BI |
|---|---|---|---|---|---|---|
| Pt-ZSM-12 | 40 | — | 125 | 2 | 10 | 33 |
| Pd-ZSM-12 | 40 | — | 125 | 2 | 10 | 40 |
| Ni-ZSM-12 | 40 | — | 125 | 2 | 10 | 88 |
| Co—Fe-ZSM-12 | — | 40 | 125 | 2 | 10 | 103 |
| Pt—Fe-X | — | 5 | 120 | 1 | 8 | 141 |

-continued

| Catalyst | Si/Al | Si/Fe | T°C. | LHSV | B/O | BI |
|---|---|---|---|---|---|---|
| Pd-Y | 5 | — | 120 | 1 | 8 | 52 |
| Co-X | 5 | — | 120 | 1 | 8 | 68 |
| Ni-Y | 5 | — | 120 | 1 | 8 | 79 |
| Pt-Mord. | 12 | — | 120 | 1 | 8 | 49 |
| Pt—Fe-beta | — | 105 | 110 | 1 | 10 | 182 |
| Ni-beta | 105 | — | 110 | 1 | 10 | 74 |
| Co-mord. | 105 | — | 110 | 1 | 10 | 293 |
| Pd-mord. | 105 | — | 110 | 1.5 | 10 | 164 |

EXAMPLE 5

This example illustrates the use of zeolites wherein the transition metal occurs mainly as an ingredient of the lattice framework and not as a component occluded in the porous cavities of the zeolite. The process was carried out under the conditions of Example 4.

| Catalyst | Si/M | T°C. | LHSV | B/O | BI |
|---|---|---|---|---|---|
| Fe-ZSM-12 | 40 | 125 | 1 | 10 | 58 |
| Fe-Y | 8 | 140 | 1 | 10 | 37 |
| Fe-mord. | 15 | 140 | 1 | 10 | 142 |
| Fe-beta | 62 | 150 | 1 | 10 | 85 |

EXAMPLE 6

This example illustrates that linear alkylbenzenes can be produced with high selectivity in a zeolite containing transition metals and in the presence of hydrogen where there is stepwise addition of the linear olefin. Experiments were carried out as in Example 1. The catalyst was Pt-ZSM-12. The preparation of LAB with staged addition of the linear olefins was carried out as follows. The reaction was carried out in five steps with equal amounts of linear olefins added in each of the five steps. The product from each step was collected for further reaction in the next step at a higher temperature. The results are summarised below. Pressure was 20 bar. H/O=3 (overall).

| Step | 1 | 2 | 3 | 4 | 5 |
|---|---|---|---|---|---|
| Temp. °C. | 115 | 120 | 125 | 128 | 135 |
| % olefin added | 20 | 20 | 20 | 20 | 20 |
| BI | 28 | 27 | 32 | 22 | 18 |

We claim:

1. A process for the production of linear alkylbenzenes which process comprises co-feeding a mixture of benzene, linear olefins and molecular hydrogen into contact with a catalyst containing a transition metal selected from the group consisting of iron, cobalt, nickel, platinum, palladium, iridium, and mixtures thereof in intimate contact with a zeolite selected from the group consisting of mordenite, beta, S, Y, and ZSM-12 at a temperature in the range of 100 to 200 degrees C., a pressure in the range of 1 to 20 bar and a liquid hourly space velocity in the range of 1 to 10, whereby the alkylbenzenes are produced in the presence of molecular hydrogen and the transition metal and said catalyst is inhibited from undergoing deactivation, and separating the linear alkylbenzenes from the reactor effluents.

2. A process according to claim 1, wherein the linear olefins contain from 8 to 20 carbon atoms.

3. A process according to claim 1, wherein the metal is incorporated into the lattice of the zeolite.

4. A process according to any of claim 1, wherein the metal is occluded in the porous cavities of the zeolite.

5. A process according to any of claim 1, wherein a major portion of the cation sites in the zeolite are occupied by hydrogen ions and/or rare-earth ions.

6. A process according to claim 1, wherein the transition element comprises from 0.005 to 5.0% wt. of the catalyst composition.

7. The process according to claim 1, wherein there are two or more catalyst beds or reactors in series and at least a portion of the linear olefin is added between the catalyst beds or reactors.

8. A process as claimed in claim 1 wherein the linear olefins include diolefins, and the molecular hydrogen suppresses formation on said catalyst of carbonaceous deposits from said diolefins without substantially hydrogenating the linear olefins to linear parafins.

9. In a process for the production of linear alkylbenzenes wherein a zeolite catalyst is contacted with a reaction medium comprising a mixture of benzene and linear olefins, and wherein the zeolite catalyst is effective to catalyze the production of the linear alkylbenzenes for a limited cycle length without needing regeneration, the improvement comprising including hydrogen in the reaction medium and a transition metal in intimate contact with the zeolite catalyst, said hydrogen being present in the reaction medium and said transition metal being present in intimate contact with the zeolite catalyst in amounts such that the cycle length in which said zeolite catalyst is effective to catalyze the production of the linear alkylbenzenes is increased.

\* \* \* \* \*